United States Patent [19]

Tseng et al.

[11] 3,931,293

[45] *Jan. 6, 1976

[54] PROCESSES FOR PRODUCING CIS ALKYL-2-METHYL-3-PENTENOATES AND ISOMER MIXTURES CONTAINING HIGH PROPORTIONS OF CIS ALKYL-2-METHYL-3-PENTENOATES

[75] Inventors: Ching Y. Tseng, Middletown; John B. Hall, Rumson; Manfred Hugo Vock, Locust; Joaquin F. Vinals, Red Bank, all of N.J.; Edward J. Shuster, Brooklyn, N.Y.

[73] Assignee: International Flavors & Fragrances Inc., New York, N.Y.

[ * ] Notice: The portion of the term of this patent subsequent to Jan. 6, 1992, has been disclaimed.

[22] Filed: July 22, 1974

[21] Appl. No.: 490,719

[52] U.S. Cl............... 260/486 R; 131/17; 131/144; 252/89; 252/132; 252/522; 260/526 N; 260/654 R; 426/65; 426/175; 426/534
[51] Int. Cl.²......................................... C07C 69/54
[58] Field of Search............................... 260/486 R

[56] References Cited
OTHER PUBLICATIONS
March, J. "Adv. Org. Chem.," McGraw-Hill, pp. 577–578 and p. 689.

Primary Examiner—Lorraine A. Weinberger
Assistant Examiner—P. J. Killos
Attorney, Agent, or Firm—Arthur L. Liberman, Esq.; Harold Haidt, Esq.

[57] ABSTRACT

Methods for producing cis-alkyl-2-methyl-3-pentenoates and isomeric mixtures containing high proportions (greater than 50%) of cis $C_2$–$C_6$ alkyl-2-methyl-3-pentenoates.

1 Claim, No Drawings

PROCESSES FOR PRODUCING CIS ALKYL-2-METHYL-3-PENTENOATES AND ISOMER MIXTURES CONTAINING HIGH PROPORTIONS OF CIS ALKYL-2-METHYL-3-PENTENOATES

BACKGROUND OF THE INVENTION

The present invention relates to cis-2-alkyl-3-pentenoates and novel isomeric mixtures containing greater than 50% cis $C_2$–$C_6$ alkyl-2-methyl-3-pentenoates produced by novel processes and compositions using such mixtures of isomers of alkyl-2-methyl-3-pentenoates to alter the flavor and/or aroma of consumable materials.

There has been considerable work performed related to substances which can be used to impart (or enhance) flavors to (or in) various consumable materials. These substances are used to diminish the use of natural materials, some of which may be in short supply and to provide more uniform properties in the finished product. Fruity, sweet, fresh, berry, pineapple, green, herbaceous, strawberry and pear aromas, as well as fruity, berry, woody, green and pear tastes are particularly desirable for many uses in foodstuff flavors. Fruity, peppery, woody, green, herbaceous, strawberry and chamomile notes and nuances are desirable in perfume compositions. Notes having Turkish-like characteristics, as well as aromatic, sweet and bitter notes are desirable in tobacco-flavoring compositions.

U.S. Pat. No. 3,449,769 issued on Mar. 10, 1970 discloses processes for imparting a fresh fruity flavor (particularly strawberry flavor) to foods by adding a small amount of 2-methyl-2-pentenoic acid to the foodstuff. In U.S. Pat. No. 3,499,769 it is emphasized that the basic nuance imparted by 2-methyl-2-pentenoic acid is a "berry" flavor. Quite unexpectedly, the novel "high cis" isomeric mixtures of the instant invention has properties different in kind from the 2-methyl-2-pentenoic acid of U.S. Pat. No. 3,499,769, which is only fruity and strawberry like, but does not have the sweet, pineapple, green, herbaceous and pear aroma and taste qualities of the isomeric ester mixture of the instant invention nor does it have the chamomile muances so useful in perfumes. Isomeric ("cis" and "trans") mixtures of 2-methyl-3-pentenoic acid are disclosed in co-pending application for U.S. letters patent, Ser. No. 408,854 filed on Oct. 23, 1973, now abandoned to have the following organoleptic properties:

a. In food flavorings, a sweet, fruity, strawberry, winey-cognac, butter-like, rum-like and butterscotch aroma and a sweet, strawberry, nutty-coconut, fatty, butter-like, rum-like and butterscotch-like taste with fruity, coconut-like isovaleric undertones;

b. In perfumes, green, sweet, sharp strawberry notes; and c. In tobaccos, aromatic, sweet, bitter, slightly woody and smokey notes giving tobacco a "Turkish-like" character.

Isomeric mixtures of 2-methyl-3-pentenoic acid are shown to be prepared by Boorman and Linstead, J.Chem.Soc. 1935, 258-67 (abstracted by Chem. Abstracts, Vol. 29, pages 2912 (7/8). 2-Ethyl-3-pentenoic acid is shown to be prepared by Fichter and Obladen, Berichte, 42, 4703-7 by distillation of alpha-ethyl gamma methyl paraconic acid which, in turn, is formed by reduction using a sodium-mercury amalgam of ethyl-alpha-ethyl aceto-succinate. The above-disclosed processes produce isomer mixtures which are considered to be different in kind insofar as their organoleptic properties are concerned from the isomer mixtures produced by the processes of the instant invention.

Ethyl-2-methyl-3-pentenoate (95% 3:1 trans:cis and 5% ethyl-2-methyl-2-pentenoate) is being offered as a development chemical by Toray Industries, Inc. of 2, Nihonbashi-Muromachi 2-chome, Chuo-Ku, Tokyo, Japan. This mixture of esters is not found to be of interest as a flavor material.

McGreer, et al, Can. J. Chem., 41, 726-31 (1963) discloses the production of various alkyl esters of pentenoic and butenoic acids by means of pyrolysis of 3,5-dimethyl-3-carbomethoxy $\Delta^1$-pyrazoline. Thus, on page 728 of the McGreer article, products having the following structures are shown to be produced:

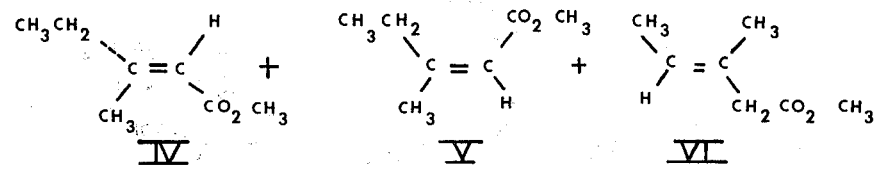

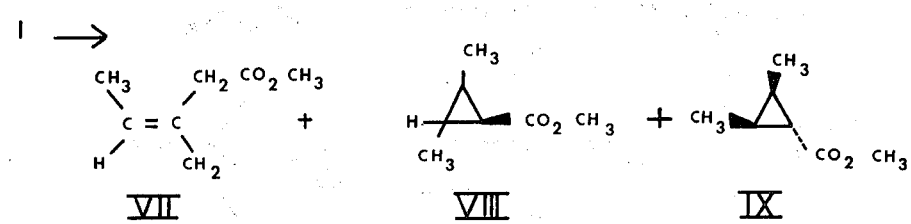

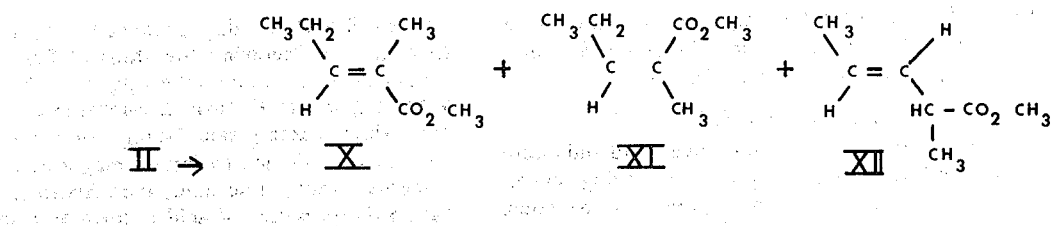

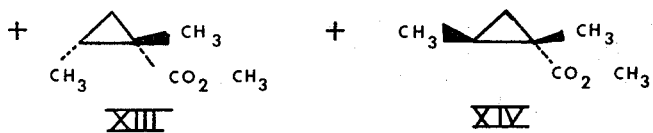

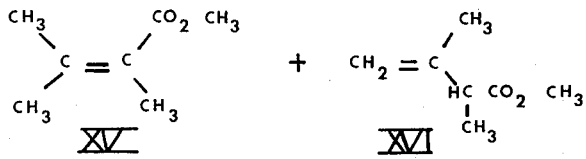

III →

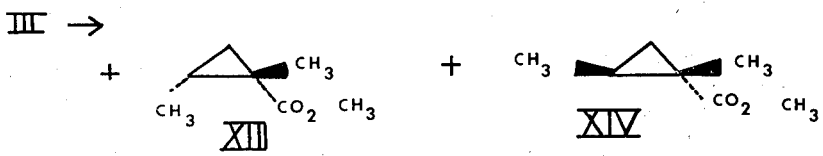

Tsuji, et al, J.Am.Chem.Soc., 86, (20) 4350–3 (1964) discloses the production of alkyl alkenoates by means of reaction of carbon monoxide, alkenyl halides and alkanols with use of palladium chloride as a catalyst. Other methods for the synthesis of alkyl alkenoates are set forth in the following references:

i. French Pat. No. 1,389,856, issued Feb. 19, 1965;
ii. Brewis and Hughes, Chem. Communications (8), 157–8 (1965);
iii. Bordenca and Marsico, Tetrahedron Letters (16), 1541–3 (1967); and
iv. Hosaka and Tsuji, Tetrahedron, 27, (16) 3821–9 (1971).

None of the above references sets forth a process for preparing the cis isomer of an alkyl pentenoate or mixtures containing more than 50% cis isomer.

Felkin, et al, Ann.Chem. (Paris) 6 (1), 17–26 (1971) discloses processing for producing "high cis" and "high trans" methyl-2-methyl-3-pentenoate mixtures, according to the following reaction sequences:

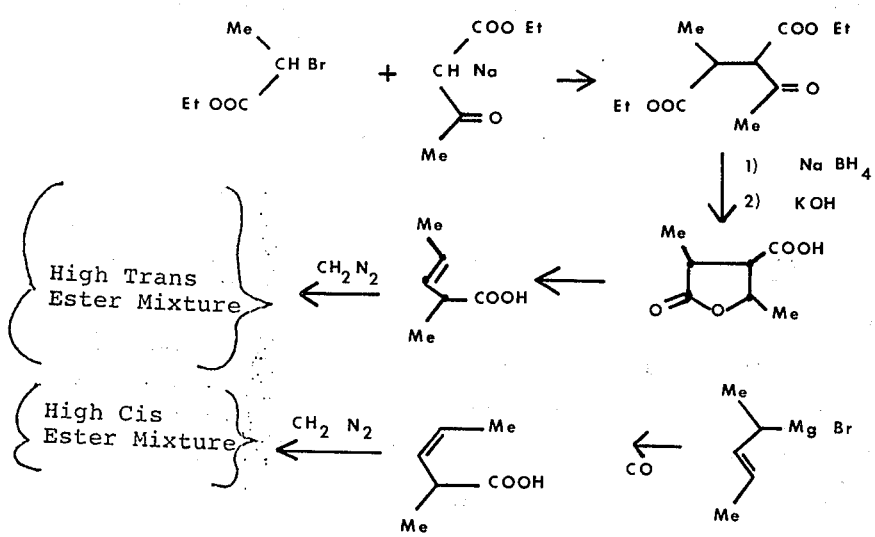

A process for preparing the "high cis" acid mixture is set forth in Felkin, et al., Chemical Communications, No. 802, pages 75 and 76 (Dec. 29, 1965).

THE INVENTION

It has now been discovered that novel solid and liquid foodstuff and flavoring compositions having sweet, fruity, fresh, berry, pineapple, green, herbaceous, strawberry and pear-like aromas and fruity, berry, woody, green, pear taste notes; and novel perfume compositions having fruity, peppery, woody, green, herbaceous, strawberry and chamomile notes, as well as novel tobacco flavoring compositions capable of imparting a Turkish-like character to tobacco and having aromatic, sweet, and bitter notes may be provided by the utilization of cis alkyl esters of 2-methyl-3-pentenoic acid and isomer mixtures of alkyl-2-methyl-3-pentenoates containing greater than 50% cis isomer having the generic formula:

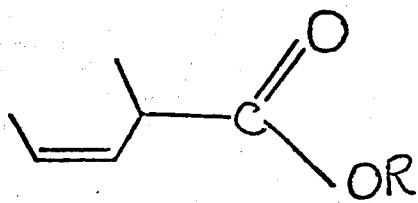

wherein R is $C_2$–$C_6$ alkyl produced either (i) according to a process involving the steps of first preparing a 2-halo-3-pentene; then admixing said 2-halo-3-pentent with magnesium to form a 2-magnesium halo-3-pentene; then reacting said 2-magnesium halo-3-pentene with carbon dioxide to form a magnesium halo salt of 2-methyl-3-pentenoic acid; then hydrolyzing the said salt in the presence of acid to form an isomer mixture containing an approximate ratio of 60% cis 2-methyl-3-pentenoic acid and 40% trans-2-methyl-3-pentenoic acid; and finally, esterifying this mixture of isomers of cis and trans-2-methyl-3-pentenoic with an alkyl halide in basic media to form a C₂–C₆ alkyl-2-methyl-3-pentenoate isomer mixture, or (ii) first reacting methyl acetylene with a methyl magnesium halide to form a methylacetylene magnesium halide Grignard reagent; then reacting the methyl acetylene magnesium halide Grignard reagent with acetaldehyde to form a 3-pentyn-2-ol magnesium halide salt; then hydrolyzing the magnesium halide salt to form 3-pentyne-2-ol; then halogenating the 3-pentyne-2-ol to form a 4-halo-2-pentyne; then reacting magnesium with the 4-halo-2-pentyne to product a 4-magnesium halo-2-pentyne Grignard reagent; then reacting the 4-magnesium halo-2-pentyne Grignard reagent with carbon dioxide to form a magnesium halo-carboxylate salt mixture of compounds having the structures:

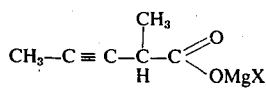

and

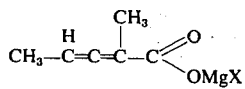

(wherein X is halogen); then hydrolyzing the magnesium halo-carboxylate salt mixture to form a mixture of carboxylic acids having the structures:

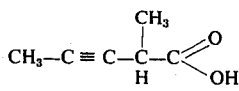

and

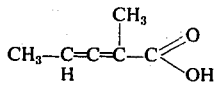

then hydrogenating the aforementioned mixture of carboxylic acids to form a mixture containing 80% cis-2-methyl-3-pentenoic acid and 20% 2-methyl-2-pentenoic acid; then esterifying this mixture of pentenoic acids with an alkyl halide in the presence of an alkali metal hydroxide and in a solvent selected from the group consisting of hexamethyl phosphoramide, a dilower alkyl formamide and dimethyl sulfoxide; and then, optionally, separating the resulting esters to yield a substantially pure cis-alkyl-2-methyl-3-pentenoate.

The term "cis-alkyl-2-methyl-3-pentenoate," as well as the structure:

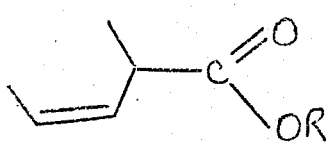

is intended herein to cover one or both stereoisomers of such material, to wit the stereoisomer having the structure:

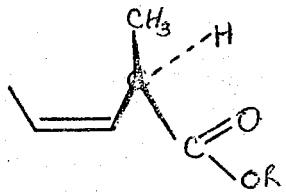

as well as the stereoisomer having the structure:

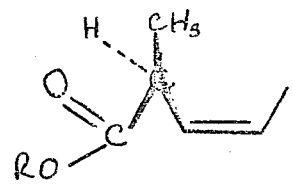

wherein R is C₂–C₆ lower alkyl. Further stereoisomers are possible depending upon the stereochemistry of the moiety, "R."

The cis-2-methyl-3-pentenoic acid alkyl esters and isomer mixtures containing same of our invention are capable of supplying and/or potentiating certain flavor and aroma notes usually lacking in many fruit flavors as well as Turkish tobacco flavors heretofore provided. Furthermore, the cis-alkyl-2-methyl-3-pentenoates and isomer mixtures containing same of our invention are capable of supplying certain fragrance notes usually lacking in many perfumery materials, for example, raspberry and strawberry fragrances.

One novel process for producing one of the novel isomer mixtures of alkyl-2-methyl-3-pentenoates containing approximately a 60:40 cis:trans isomer ratio of same involves the steps of:

a. First preparing a 2-halo-3-pentene by intimately admixing either hydrogen chloride or hydrogen bromide with 1,3-pentadiene at a temperature of from −20°C up to +30°C, preferably, from 0° up to 10°C and at a pressure, preferably, of atmospheric pressure. The 1,3-pentadiene (otherwise known as "piperylene" preferably has a purity of 90% but 50% piperylene may also be used. The 2-halo-3-pentene thus produced may be used in its crude form without further purification in subsequent reactions;

b. The 2-halo-3-pentene is then reacted with magnesium to form a Grignard reagent, otherwise known as 2-magnesium halo-3-pentene. The reaction with the magnesium is carried out preferably in the presence of tetrahydrofuran, however, other solvents such as diethyl ether may also be used. The mole ratio of magnesium to halo-pentene is preferably from 1 up to 10 moles of magnesium per mole of halo-pentene, more preferably, from 3 up to 5 moles of magnesium per mole of halo-pentene. The temperature of reaction is from 10 up to 50°C; preferably from 10° up to 20°C. Temperatures lower than 10°C give rise to a reaction rate which is too slow to be economical. Temperatures higher than 50°C give rise to side reactions causing an undue lowering of the yield of product;

c. The Grignard reagent produced in step (b) is then reacted with carbon dioxide (preferably in the form of crushed dry ice). The reaction with carbon dioxide may also be carried out by bubbling carbon dioxide into the Grignard reagent at atmospheric pressure at a temperature of between −20°C up to +40°C, preferably from 0°C to 20°C or reacting the Grignard reagent with gaseous carbon dioxide at higher pressures of from 10 up to 100 pounds per square inch absolute at temperatures up to 50°C. When the reaction takes place with crushed dry ice, the temperature is the temperature of crushed dry ice. The carbonation forms the magnesium halo salt of 2-methyl-3-pentenoic acid having the structure:

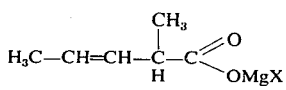

wherein X is halogen selected from the group consisting of chlorine and bromine;

d. Hydrolysis of the magnesium halo salt of 2-methyl-3-pentenoic acid in acid at a pH of from 2 up to 3. The preferred acid is a mineral acid such as hydrochloric acid or sulfuric acid;

e. Esterifying the resultant 2-methyl-3-pentenoic acid with an alkyl halide of the formula RX wherein R is $C_2$–$C_6$ alkyl and X is chloro, bromo or iodo, in the presence of an equivalent amount of base (e.g., 50% aqueous sodium hydroxide, potassium hydroxide sodium carbonate, sodium bicarbonate or lithium hydroxide) and in the presence of a solvent, for example, hexamethyl phosphoramide, a dilower alkyl fromamide, such as dimethyl formamide and dimethyl sulfoxide, at a temperature in the range of 0°C–50°C ("room temperature", 20°–30°C is preferred). The solvent ratio is in the range of from 300 g up to 900 g of solvent per mole of 2-methyl-3-pentenoic acid used with a preferred ratio of 600 g of solvent per mole of 2-methyl-3-pentenoic acid. The reaction rate is inversely proportional to the temperature of reaction; however, too high a temperature leads to isomerization of the reaction product. The reaction time can range from 2 up to 50 hours.

f. Optionally, the resulting 60:40 cis-trans alkyl-2-methyl-3-pentenoate mixture may be separated using GLC apparatus.

A second novel process for producing another of the novel isomer mixtures containing a high proportion of cis-alkyl-2-methyl-3-pentenoates, to wit approximately 80% cis-alkyl-2-methyl-3-pentenoate and 20% alkyl-2-methyl-2-pentenoate, involves the steps of:

a. First preparing a methyl acetylene magnesium halide Grignard reagent by admixing, a methyl magnesium halide (the chloride, bromide or iodide) with a slight molar excess of methyl acetylene (preferably as "Mapp Gas", a commercial mixture of methyl acetylene and allene) at a temperature in the range of 40°–60°C (preferably 40°–50°C) in an inert solvent such as tetrahydrofuran or diethyl ether. Preferably, the reaction time range is from 4–12 hours;

b. Preparing 3-pentyne-2-ol by first admixing the methyl magnesium halide reaction product preferably in its original reaction solvent with a slight molar excess of acetaldehyde to form a magnesium halo salt of 3-pentyne-2-ol, at a temperature in the range of 20°–30°C and then hydrolyzing the said magnesium halo salt of 3-pentyne-2-ol, preferably with a cold concentrated mineral acid such as concentrated hydrochloric acid in ice, and purifying the resulting 3-pentyn-2-ol using standard physical separation techniques, e.g., extraction and distillation;

c. Preparing a 4-halo-2-pentyne (e.g., 4-chloro-2-pentyne or 4-bromo-2-pentyne) by means of halogenating the 3-pentyn-2-ol with a slight molar excess halogenating agent, e.g., phosphorous trichloride, phosphorous tribromide, and $SOCl_2$, at temperatures in the range of 20°–80°C, depending upon the halogenation reagent used. The preferred halogenating reagent is $PCl_3$ using a temperature range of 20°–25°C;

d. Preparing a 4-magnesium-halo-2-pentyne Grignard reagent by reaction of the 4-halo-2-pentyne with magnesium in a solvent, for example, tetrahydrofuran or diethyl ether at a temperature in the range of 25°–50°C, depending upon the solvent used;

e. Preparing a magnesium halo carboxylate salt mixture of compounds having the structures:

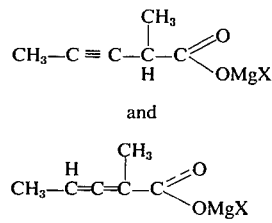

and (wherein X is halogen, e.g., chloro or bromo) by intimately admixing carbondioxide (either in the gas phase, or as a solid in the form of powdered dry ice). The reaction with carbondioxide may be carried out by bubbling carbon dioxide into the Grignard reagent at atmospheric pressure at a temperature of between −20°C up to +40°C, preferably, from 0°C to 20°C or reacting the Grignard reagent with gaseous carbon dioxide at higher pressures of from 10 up to 1,000 pounds per square inch absolute at temperatures up to 50°C. When the reaction takes place with crushed dry ice, the temperature is the temperature of crushed dry ice.

f. Hydrolyzing the resulting magnesium halocarboxylate salt mixture with aqueous mineral acid (e.g., hydrochloric acid) at a temperature in the range of 20°–30°C to produce a crude mixture of
  i. 2-methyl-3-pentynoic acid; and
  ii. 2-methyl-2,3-pentadienoic acid in a (i):(ii) ratio of 3:1;

g. Preparing a mixture containing about 80% cis-2-methyl-3-pentenoic acid and 20% 2-methyl-2-pentenoic acid by hydrogenating the mixed acid product of step (f) supra in the presence of a palladium/$CaSO_4$ catalyst containing 3% Pd at a pressure in the range of 10–100 psig; preferably in the range of 20–40 psig; preferably in a lower alkanol solvent such as methanol or ethanol at a temperature in the range of 20°–40°C, preferably 20°–25°C. The weight percent range of catalyst is from 0.05% up to 1.5% with a range of 0.1% up to 1% being preferred. The resulting acid reaction product may then be purified using standard physical separation techniques, e.g., extraction and distillation;

h. Esterifying the resultant mixture containing 80% cis-2-methyl-3-pentenoic acid and 20% 2-methyl-2-pentenoic acid with an alkyl halide of the formula RX wherein R is $C_2$–$C_6$ alkyl and X is chloro, bromo or iodo, in the presence of an equivalent amount of base (e.g., 50% aqueous sodium hydroxide, potassium hydroxide, sodium bicarbonate, sodium carbonate or lithium hydroxide) and in the presence of a solvent, for example, hexamethyl phosphoramide, a dilower alkyl formamide such as dimethyl formamide and dimethyl sulfoxide, at a temperature in the range of 0°–50°C ("room temperature", 20°–30°C is preferred). The solvent ratio is in the range of from 300 g up to 900 g of solvent per mole of 2-methyl-3-pentenoic acid used with a preferred ratio of 600 g of solvent per mole of acid reactant. The reaction rate is inversely proportional to the temperature of reaction; however, too high a temperature leads to isomerization of the reaction product. The reaction time can range from 2 up to 50 hours.

i. Optionally, the resulting ester mixture may be separated using GLC apparatus.

Examples of specific alkyl halide reactants, reaction products and organoleptic characteristics of such reaction products, are set forth in the following table:

| Alkyl Halide | Reaction Product | Organoleptic Properties |
| --- | --- | --- |
| Ethyl Bromide | Ethyl-2-methyl-3-pentenoate (cis: trans ratio, approximately 3:2) | Fruity, fresh, pineapple, strawberry aroma and sweet, fruity, pineapple, strawberry, mellon-green taste at 1 ppm. Also a fruity, green, strawberry fragrance note with a chamomile nuance. |
| Isopropyl Bromide | Isopropyl-2-methyl-3-pentenoate (cis: trans ratio, approximately 3:2) | A fruity, characteristic strawberry taste and a sweet, astringent after-taste at 5 ppm; and a fruity, herbaceous fragrance note. |
| Isobutyl Bromide | Isobutyl-2-methyl-3-pentenoate (cis: trans ratio, approximately 3:2) | Characteristic sweet, strawberry taste, with lasting strawberry after-taste at 5 ppm; at 10 ppm, characteristic sweeter strawberry taste with a lasting sweet strawberry after taste. Also a fruity, woody fragrance note. |
| n-Hexyl Bromide | n-Hexyl-2-methyl-3-pentenoate (cis: trans ratio, approximately 3:2) | A pear, strawberry, fruity aroma and a sweet, strawberry, pear, fruity taste at 2 ppm. In addition, fruity, peppery, chamomile and floral fragrance notes. |

When the cis-alkyl-2-methyl-3-pentenoate or isomer mixture containing more than 50% of same of our invention hereinafter called "high cis alkyl-2-methyl-3-pentenoate" is used as a food flavor adjuvant, the nature of the co-ingredients included with the said high cis alkyl-2-methyl-3-pentenoate in formulating the product composition will also serve to alter the organoleptic characteristics of the ultimate foodstuff treated therewith. As used herein in regard to flavors, the term "alter" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste." As used herein, the term "foodstuff" includes both solid and liquid ingestible materials which usually do, but need not, have nutritional value. Thus "foodstuffs" include soups, convenience foods, beverages, dairy products, candies, vegetables, cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in the selection thereof. Accordingly, such materials which may, in general, be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar; carrageenan; cellulose and cellulose derivatives, such as carboxymethyl cellulose and methyl cellulose; natural and synthetic gums such as gum arabic, gum tragacanth; gelatin, proteinaceous materials; lipids; carbohydrates; starches, pectins and emulsufiers, e.g., mono-and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mon- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers; anti-caking agents, e.g., aluminum calcium sulfate and tribasic calcium phospate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenal, cis-3-hexenal, 2-heptanone, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha terpineol, cis-terpineol hydrate; esters, such as butyl acetate, ethyl acetate, ethyl acetoacetate, ethyl benzoate, ethyl butyrate, ethyl capronate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the high cis alkyl-2-methyl-3-pentenoate can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of high cis-alkyl-2-methyl-3-pentenoate employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing a composition merely deficient in natural flavor or aroma. Thus, the primary requirement is that the amount selected should be "effective," i.e., sufficient to alter the organoleptic characteristics of the parent composition, whether foodstuff per se or flavoring composition. Thus, the use of insufficient quantities of high cis-alkyl-2-methyl-3-pentenoate will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of high cis-alkyl-2-methyl-3-pentenoates ranging from a small but effective amount, e.g., 0.10 parts per million up to about 50 parts per million by weight based on total composition are suitable. Concentrations in excess of the maximum quantity stated are not normally recommended since they fail to provide commensurate enhancement of organoleptic properties. In those instances wherein the high cis-alkyl-2-methyl-3-pentenoate is added to the foodstuff as an integral component of a flavoring composition, it is of course essential that the total quantity of flavoring composition employed be sufficient to yield an effective high cis-alkyl-2-methyl-3-pentenoate concentration in the foodstuff product.

Food flavoring compositions prepared in accordance with the present invention preferably contain the high cis-alkyl-2-methyl-3-pentenoate in concentrations ranging from about 0.05% up to about 10% by weight based on the total weight of said flavoring composition.

The compositions described herein can be prepared according to conventional techniques well known, as typified by cake batters and vegetable juices, can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the high cis-alkyl-2-methyl-3-pentenoate with, for example, gum arabic, gum tragacanth, carrageenan and the like, and thereafter spray-drying the resultant mixture whereby to obtain the particular solid product. Pre-prepared flavor mixes in powder form, e.g., a strawberry-flavored powder mix or a raspberry-flavored powder mix are obtained by mixing the dried solid components, e.g., starch, sugar and the like and the high cis-alkyl-2-methyl-3-pentenoate in a dry blender until the requisite degree of uniformity is achieved.

It is presently preferred to combine with the high cis-alkyl-2-methyl-3-pentenoate the following adjuvants:

Parahydroxy benzyl acetone
Vanillin
Maltol
Ethyl-3-methyl-3-phenyl glycidate
Benzyl acetate
Ethyl butyrate
Methyl cinnamate
Methyl anthranilate
Alpha-ionone
Gamma-undecalactone
Diacetyl
Anethole
Cis-3-hexenol
2-(4 hydroxy-4-methyl pentyl) norbornadiene (prepared according to Example II of application for U.S. patent Ser. No. 461,703 filed on Apr. 17, 1974)
Beta-ionone
Isobutyl acetate
Dimethyl sulfide
Acetic acid
Acetaldehyde
4-(2,6,6-trimethyl-1,3-cyclohexadiene-1-yl)-2-butanone (prepared according to Example XVI of application for U.S. patent Ser. No. 386,320 filed on Aug. 7, 1973)
4-(6,6-dimethyl-2-methylene-3-cyclohexen-1-yl)-2-butanone (prepared according to Example XVI of application for U.S. patent Ser. No. 386,320 filed on Aug. 7, 1973)
Geraniol
Ethyl pelargonate
Isoamyl acetate
Naphthyl ethyl ether
Ethyl acetate
Isoamyl butyrate
2-Methyl-2-pentenoic acid
2-Methyl-3-pentenoic acid Elemecine (4-allyl-1,2,6-trimethoxy benzene)
Isoelemecine (4-(1-propenyl)-1,2,6-trimethoxy benzene)

The high cis-alkyl-2-methyl-3-pentenoate can also be used to improve and augment the organoleptic properties of tobacco and tobacco products. Thus, the said high cis-alkyl-2-methyl-3-pentenoate will impart a Turkish-like character to tobacco (in smoke flavor) when used at levels of from 50 parts per million up to 500 parts per million based on the dry weight of the tobacco. "Tobacco," as used herein, includes natural tobaccos such as burley, Turkish tobacco, Maryland tobacco, tobacco-like products such as reconstituted tobacco or homogenized tobacco and tobacco substitutes intended to replace natural tobacco such as various vegetable leaves, for example, lettuce, cabbage leaves and the like.

One or more of the high cis-2-methyl-3-pentenoates of our invention and an auxiliary perfume ingredient, including, for example, one or more alcohols, aldehydes, nitriles, esters, cyclic esters and natural essential oils, may be admixed so that the combined odors of the individual components produce a pleasant and desired fragrance, particularly and preferably in strawberry or raspberry fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, each of the individual components will contribute its particular olfactory characteristics, but the over-all effect of the perfume composition will be the sum of the effects of each of the ingredients. Thus one or more of the alkyl-2-methyl-3-pentenoate isomer mixtures of our invention can be used to alter the aroma characteristics of a perfume composition, for example, by utilizing or moderating the olfactory reaction contributed by another ingredient in the composition.

The amount of high cis-alkyl-2-methyl-3-pentenoate of our invention which will be effective in perfumed articles, perfume compositions or perfumed compositions depends on many factors, including the other ingredients, their amounts and the effects which are desired. It has been found that perfume compositions containing as little as 0.3% of high cis-alkyl-2-methyl-3-pentenoate, or even less (e.g., 0.05%), can be used to impart a scent odor to soaps, cosmetics, or other products. The amount employed can range up to 100% of the fragrance components and will depend on considerations of cost, nature of the end product, the effect desired on the finished product and the particular fragrance sought.

One or more of the high cis-alkyl-2-methyl-3-pentenoate isomer mixtures of our invention is useful by themselves or in perfume compositions such as an olfactory component in detergents, and soaps; space odorants and deodorants, perfumes, colognes, toilet water, bath preparations, such as bath oils and bath solids; hair preparations, such as lacquers, brilliantines, pomades and shampoo; cosmetic preparations, such as creams, deodorants, hand lotions, and sun screens; powders, such as talcs, dusting powders, face powders and the like. When used as a olfactory component of a perfumed article, as little as 100 parts per million the high cis-alkyl-2-methyl-3-pentenoate will suffice to impart a fruity, green, strawberry note with chamomile nuances; or fruity herbaceous notes or fruity, peppery chamomile, floral notes, all of which are key odor characteristics of strawberry and/or raspberry perfume formulations. Generally, no more than 2.0% of the high cis-alkyl-2-methyl-3-pentenoate, based on the ultimate end product, is required in the perfume composition.

In addition, the perfumed article, perfume composition, perfumed composition or fragrance composition of our invention can contain a vehicle or carrier for the high cis-alkyl-2-methyl-3-pentenoate. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that one or more of the high cis-alkyl-2-methyl-3-pentenoate of our invention can be utilized to alter the sensory properties, particularly organoleptic properties, such as flavor and/or fragrance of a wide variety of consumable materials.

The following examples are given to illustrate embodiments of the invention as it is presently preferred to practice it. It will be understood that these examples are illustrative, and the invention is not to be considered as restricted thereto except as indicated in the appended claims. All parts and percentages set forth herein are by weight unless otherwise specified.

EXAMPLE I

Preparation of an Approximately 60:40 Cis:Trans Mixture 2-Methyl-3-Pentenoic Acid A. Preparation of 4-Chloro-2-Pentene Into a 3 liter flask equipped with stirrer, thermometer, reflux condenser, subsurface addition tube and inlet and outlet bubblers and cooling bath, 1000 gms (14.8 moles) of 97.7% pure piperylene is charged. The piperylene is cooled to 10°C and the reaction vessel is purged with dry nitrogen. While passing in hydrogen chloride, the reaction mass is stirred vigorously and the reaction mass temperature is maintained at 10°–15°C with external cooling. The hydrogen chloride is added over a period of 7 hours. The reaction mass is then purged with nitrogen at room temperature for a period of 10–20 minutes to remove any excess hydrogen chloride. The crude product may then be used further without purification for the preparation of the 2-methyl-3-pentenoic acid isomer mixture. The amount of crude product obtained is 1,435 gms.

B. Preparation of 2-Methyl-3-Pentenoic Acid Isomer Mixture

Into a 12 liter reaction vessel equipped with stirrer, thermometer, reflux condenser, dropping funnel, two bubblers, heating mantle and cooling bath, thoroughly purged with nitrogen, the following materials are charged:

| | |
|---|---|
| Magnesium Turnings | 600 gms |
| Tetrahydrofuran | 3 liters |

The magnesium-tetrahydrofuran mixture is heated to 50°C at which time 70 ml of a solution (produced by admixing 750 gms of 4-chloro-2-pentene produced in step (A) with 2 liters of tetrahydrofuran) is added to the magnesium-tetrahydrofuran mixture in the 12-liter reaction vessel with stirring. The reaction mass temperature increases indicating the initiation of a Grignard reaction. With stirring, the remainder of the 4-chloro-2-pentene-tetrahydrofuran solution is added over a period of 5 hours. During the first 30 minutes of the addition, the reaction mass is slowly cooled to 25°–30°C and after that time the reaction mass is maintained at 25°–30°C throughout the remainder of the addition. The reaction mass is then stirred for 1 hour at 25°–30°C.

7.2 Kilograms of finely crushed dry ice is added into a 22 liter reaction flask equipped with an air driven motor stirrer, addition tube and an inlet and outlet bubblers. The Grignard reagent produced in the 12 liter reaction vessel is siphoned onto the dry ice in the 22 liter flask thus leaving the excess magnesium turnings in the 12 liter flask. A nitrogen stream is used to prevent premature reaction of carbon dioxide at the inlet tube. The dry ice-Grignard reagent mixture is then stirred slowly until the excess carbon dioxide has evaporated. The time of stirring is 8 hours. 2.5 Liters of water is then added to dissolve the magnesium salt and tetrahydrofuran is recovered by distillation at atmospheric pressure to a pot temperature of 80°C. 1.25 Liters of toluene is then added to the reaction mass followed by 750 ml of concentrated hydrochloric acid over a period of 30 minutes maintaining the temperature of the reaction mass between 30°–40°C. The reaction mass is then stirred for another 30 minutes without further heating or cooling. The organic layer is removed and the aqueous layer is extracted with 1.25 liters of toluene after which time the two organic layers are combined. The organic solution is then stripped of solvent and the crude 2-methyl-3-pentenoic acid is rushed over to a pot temperature of 180°C at 2 mm Hg. using a 2 liter still with a 2 inch splash column. The rushed over 2-methyl-3-pentenoic acid is then fractionated at 3 mm Hg. pressure and a vapor temperature of 62°–63°C on a 1½ inch × 18 inch Goodloe packed column after adding 40 gms of Primol and 1 gm of Ionol. NMR, IR and Raman spectral analyses indicate that the material produced is a 60:40 cis: trans mixture of isomers of 2-methyl-3-pentenoic acid.

NMR Analysis: (CDCl₃)

| Signal | Interpretation |
| --- | --- |
| 1.24 (d, 3H) | —CH—C$\underline{H}_3$ |
| 1.69 (d, 3H) | =CH—C$\underline{H}_3$ |
| (3.10)<br>(m, 1H)<br>(3.50) | —C$\underline{H}$— (Shows cis:trans ratio of 3:2) |
| 5.52 ppm (m, 2H) | —C$\underline{H}$=C$\underline{H}$— |

NOTE:
Signal at 3.50 ppm attributed to "cis" isomer, and 3.10 ppm attributed to "trans" isomer.

EXAMPLE II

Preparation of (i) Mixture of 60% Cis Ethyl-2-Methyl-3-Pentenoate and 40% Trans-Ethyl-2-Methyl-3-Pentenoate and (ii) Cis Ethyl-2-Methyl-3-Pentenoate Into a 500 ml flask equipped with magnetic stirring bar, the following ingredients are added while maintaining the temperature at 20°–25°C using an ice water cooling bath and with stirring:

| (i) | 2-methyl-3-pentenoic acid 60:40 cis:trans isomer mixture (produced according to Example I) | 38 g (0.33 moles) |
| --- | --- | --- |
| (ii) | Ethyl bromide | 40 g (0.37 moles) |
| (iii) | Sodium hydroxide (50% aqueous solution) | 32 g (0.40 moles) |
| (iv) | Hexamethyl phosphoramide | 200 g |

The reaction mass is stirred for a period of 15 hours at room temperature. 300 ml water is then added to the mass and the solution is extracted with 200 ml of diethyl ether. The ether extract is washed with 20 ml of 20% sodium chloride solution, and is then concentrated by means of rotary evaporation. The resulting residue (32 grams) is distilled at 50 mm Hg. pressure with a semi-micro distillation apparatus, thereby giving 23 g of ethyl-2-methyl-3-pentenoate (chemical yield: 50%).

Boiling point: 75°C at 50 mm Hg. pressure. The ratio of cis isomer to trans isomer is 3:2.

| (A) NMR Spectrum of mixture of cis and trans isomer of ethyl-2-methyl-3-pentenoate ester (CDCl₃) | |
| --- | --- |
| Signal | Interpretation |
| 1.24 (d, 3H) | —CH—C$\underline{H}_3$ |
| 1.25 (t, 3H) | —O—C$\underline{H}_2$—CH₃ |
| 1.65 (d, 3H) | =CH—C$\underline{H}_3$ |
| (3.05)<br>(m, 1H)<br>(3.45) | —C$\underline{H}$— (Area integral indicates that cis:trans isomer ratio is 3:2) |
| 4.10 (q, 2H) | —C(=O)—O—C$\underline{H}_2$—CH₃ |
| 5.50 ppm (m, 2H) | —C$\underline{H}$=C$\underline{H}$— |

The mixture is separated using GLC trapping.

GLC CONDITIONS

Column: 20 feet × ¼ inch OD 5% OV-25 on 80/100 mesh Chromosorb G stainless steel
Flow: 100 ml/min Helium
Temperatures:
  Column = 150° isothermal
  Injector = 230°
  Detector (T.C.) = 260°

The individual NMR analyses (CDCl₃) are as follows:

(B) Cis isomer of ethyl-2-methyl-3-pentenoate: NMR Analysis (CDCl₃):

| Signal | Interpretation |
| --- | --- |
| 1.22 (d, 3H) | —CH—C$\underline{H}_3$ |
| 1.28 (t, 3H) | —CH₂—C$\underline{H}_3$ |
| 1.66 (d, 3H) | C=CH—C$\underline{H}_3$ |
| 3.44 (m, 1H) | —C$\underline{H}$— |
| 4.15 (q, 2H) | $\underset{\diagup}{\overset{O\diagdown}{C}}$—O—C$\underline{H}_2$—CH₃ |

-continued (B) Cis isomer of ethyl-2-methyl-3-pentenoate: NMR Analysis (CDCl₃):

| Signal | Interpretation |
|---|---|
| 5.52 ppm (m, 2H) | —CH=CH— |

(C) Trans isomer of ethyl-2-methyl-3-pentenoate: NMR Analysis (CDCl₃)

| Signal | Interpretation |
|---|---|
| 1.22 (d, 3H) | —CH—C$\underline{H}_3$ |
| 1.28 (t, 3H) | —CH₂—C$\underline{H}_3$ |
| 1.66 (d, 3H) | C=CH—C$\underline{H}_3$ |
| 3.10 (m, 1H) | —C$\underline{H}$— |
| 4.15 (q, 2H) | $\overset{O}{\underset{}{\diagdown}}$C—O—C$\underline{H}_2$—CH₃ |
| 5.52 ppm (m, 2H) | —CH=CH— |

EXAMPLE III

Preparation of the Esters: (i) Isopropyl-2-Methyl-3-Pentenoate: and (ii) Isobutyl-2-Methyl-Pentenoate;

Into a 250 ml flask equipped with magnetic stirring bar and operated at 20°–25°C, using external cooling, the following materials are added:

| | | |
|---|---|---|
| (i) | 2-methyl-3-pentenoic acid produced according to the process of Example I | 17.1 g (0.15 moles) |
| (ii) | Iodomethane | 4.26 g (0.03 moles) |
| (iii) | Isopropyl bromide | 3.6 g (0.03 moles) |
| (iv) | Isobutyl bromide | 4.11 g (0.03 moles) |
| (v) | Isoamyl bromide | 4.53 g (0.03 moles) |
| (vi) | Sodium hydroxide (50% aqueous solution) | 16.0 g (0.2 moles) |
| (vii) | Hexamethyl phosphoramide | 180 g |

The reaction mass is stirred for a period of 72 hours while maintaining the reaction mass temperature at 20°–25°C. At the end of the 72 hour period, the reaction mass is diluted with 100 ml of water and extracted with two 100 ml portions of diethyl ether. The diethyl ether extract is then evaporated, leaving a residue. The residue is rush-distilled at 0.3 mm Hg. pressure yielding 6 g of an oil. GLC analysis indicates at least two major and three minor components. The major components are trapped and certified by mass spectral and NMR analysis to be isopropyl-2-methyl-3-pentenoate and isobutyl-2-methyl-3-pentenoate. The GLC conditions are as follows: 100° – 200°C; 6°C/minute; ¼ inch × 10 feet — 5% carbowax packed column.

NMR Analysis (CDCl₃) for isopropyl-2-methyl-3-pentenoate (having a cis:trans mole ratio of 3:2):

| Signal | Interpretation |
|---|---|
| 1.22 (d, 9H) | —CH—C$\underline{H}_3$ |
| 1.70 (d, 3H) | =CH—C$\underline{H}_3$ |
| (3.0) (m, 1H) (3.40) | —C$\underline{H}$— (Area integral indicates that cis:trans isomer ratio is 3:2) |

-continued

NMR Analysis (CDCl₃) for isopropyl-2-methyl-3-pentenoate (having a cis:trans mole ratio of 3:2):

| Signal | Interpretation |
|---|---|
| 5.0 (m, 1H) | $\overset{O}{\diagdown}$C—O—C$\underline{H}$ |
| 5.52 ppm (m, 2H) | —C$\underline{H}$=C$\underline{H}$— |

NMR Analysis (CDCl₃) for isobutyl-2-methyl-3-pentenoate (having a cis:trans mole ratio of 3:2):

| Signal | Interpretation |
|---|---|
| 0.97 (d, 6H) | —CH—C$\underline{H}_3$ |
| 1.04 (d, 3H) | —C(=O)—CH—CH₃ |
| 1.70 (d, 3H) | =CH—C$\underline{H}_3$ |
| 1.90 (m, 1H) | —C—C$\underline{H}$— |
| (3.10) (m, 1H) (3.50) | —C(=O)—C—H (Shows that cis:trans isomer ratio is 3:2) |
| 3.88 (d, 2H) | $\overset{O}{\diagdown}$C—O—C$\underline{H}_2$— |
| 5.52 ppm (m, 2H) | —C$\underline{H}$=C$\underline{H}$— |

EXAMPLE IV

Preparation of n-Hexyl-2-Methyl-3-Pentenoate

Into a 125 ml reaction vessel equipped with magnetic stirrer and maintained at room temperature, the following materials are added:

| | | |
|---|---|---|
| (i) | 2-methyl-3-pentenoic acid isomer mixture prepared according to Example I | 1.1 g (0.01 moles) |
| (ii) | 1-bromo hexane | 2.0 g (0.012 moles) |
| (iii) | Hexamethyl phosphoramide | 20 g |
| (iv) | Sodium hydroxide (50% aqueous solution) | 1.0 g (0.012 moles) |

The reaction mass is stirred for a period of three hours at room temperature. It is then diluted with 100 ml of water and extracted with 50 ml of diethyl ether. The resulting ether extract is washed with three 10 ml portions of 20% aqueous sodium chloride solution. The ether is then evaporated to yield 2.0 g of an oil. GLC analysis indicates 67% n-hexyl-2-methyl-3-pentenoate. The mixture of esters is separated by GLC trapping.

NMR Analysis (CDCl₃) indicating that it is a mixture of cis and trans isomers with the ratio of cis isomer: trans isomer being 3:2 and is as follows:

| Signal | Interpretation |
|---|---|
| 0.90 (t, 3H) | C$\underline{H}_3$—CH₂— |
| 1.24 (d, 3H) | CH₃—CH— |
| 1.28 (m, 6H) | —C$\underline{H}_2$— |
| 1.64 (m, 5H) | —C$\underline{H}_2$—C—O and =C—CH₃ |
| (3.10) (m, 1H) (3.44) | —C$\underline{H}$— (Area integral indicates that cis:trans isomer ratio is 3:2) |

-continued

NMR Analysis (CDCl₃) indicating that it is a mixture of cis and trans isomers with the ratio of cis isomer: trans isomer being 3:2 and is as follows:

| Signal | Interpretation |
|---|---|
| 4.08 (t, 2H) | 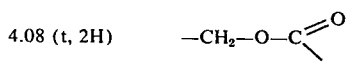 |
| 5.52 ppm (m, 2H) | —CH=CH— |

EXAMPLE V

Flavor Formulation Containing Ethyl-2-Methyl-3-Pentenoate 3:2 Cis:Trans Isomer Mixture The following basic strawberry formulation is prepared:

| Ingredient | Parts by Weight |
|---|---|
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |
| Alpha-ionone | 0.0 |
| Gamma undecalactone | 0.2 |
| Diacetyl | 0.2 |
| Anethole | 0.1 |
| Cis-3-hexenol | 1.7 |
| 95% Aqueous ethanol | 38.5 |
| Propylene glycol | 50.0 |
| | 100.0 |

To a portion of the foregoing formulation, 0.2% by weight of ethyl-2-methyl-3-pentenoate, 3:2 cis:trans isomer mixture prepared according to the process of Example II is added. The formulation with the ethyl-2-methyl-3-pentenoate is compared to the same formulation without said ethyl-2-methyl-3-pentenoate.

Both flavors are evaluated in a milk beverage sweetened with 10% sugar at the rate of 100 ppm. Both beverages are tasted by an expert panel. The beverage containing the strawberry formulation *with* the addition of ethyl-2-methyl-3-pentenoate is unanimously preferred as having a more natural like, delicate strawberry aroma, a sweeter, more pleasant, strawberry taste and a sweet, strawberry after-taste.

EXAMPLE VI

Raspberry Perfume Formulation

The following formulation is prepared:

| Ingredient | Parts by Weight |
|---|---|
| Ethyl-2-methyl-3-pentenoate 3:2 cis:trans isomer mixture prepared according to the process of Example II | 10 |
| Ethyl-3-methyl-3-phenyl glycidate | 150 |
| Vanillin | 5 |
| 3-Hydroxy-2-methyl-4-pyrone | 10 |
| Beta-ionone | 30 |
| Ethyl acetate | 1 |
| Ethyl acetoacetate | 2 |
| Diacetyl | 1 |
| Heliotropyl acetate | 50 |
| 4-(parahydroxyphenyl)-2-butanone | 50 |
| Ethyl laurate | 30 |
| Ethyl isovalerate | 10 |

-continued

| Ingredient | Parts by Weight |
|---|---|
| Ethyl butyrate | 50 |
| Cinnamyl cinnamate | 20 |
| | 419 |

The ethyl-2-methyl-3-pentenoate imparts to this raspberry perfume formulation a delicate raspberry topnote nuance.

EXAMPLE VII

Tobacco Flavor Formulation and Tobacco

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the ethyl-2-methyl-3-pentenoate 3:2 cis:trans isomer mixture produced according to the process of Example II. The control cigarettes not containing the ethyl-2-methyl-3-pentenoate isomer mixture produced according to the process of Example II and the experimental cigarettes which do contain the ethyl-2-methyl-3-pentenoate isomer mixture produced according to the process of Example II are evaluated by paired comparison, and the results are as follows:

In aroma, the cigarettes containing the ethyl-2-methyl-3-pentenoate isomer mixture have been found to be more aromatic.

In smoke flavor, the cigarettes containing the ethyl-2-methyl-3-pentenoate isomer mixture are more aromatic, more sweet, more bitter, slightly less harsh in the mouth and throat and leave a slight, sweet chemical mouth-coating effect similar to Turkish tobacco.

In summary, the ethyl-2-methyl-3-pentenoate isomer mixture enhances the tobacco-like taste and aroma of a blended cigarette and imparts to that cigarette a Turkish-like character in smoke flavor.

EXAMPLE VIII

The following concentrate is prepared:

| Ingredient | Percent |
| --- | --- |
| Geraniol | 1.00 |
| Ethyl methyl phenyl glycidate | 3.33 |
| Isopropyl-2-methyl-3-pentenoate 3:2 cis:trans isomer mixture prepared according to the process of Example III) | 4.77 |
| Vanillin | 5.66 |
| Ethyl pelargonate | 13.06 |
| Isoamyl acetate | 14.00 |
| Ethyl butyrate | 58.18 |

EXAMPLE IX

| Ingredient | Percent |
| --- | --- |
| Naphthyl ethyl ether | 0.96 |
| Vanillin | 2.66 |
| Ethyl methyl phenyl glycidate | 2.88 |
| Isobutyl-2-methyl-3-pentenoate 3:2 cis:trans isomer mixture prepared according to the process of Example III) | 4.90 |
| Ethyl acetate | 9.58 |
| Isoamyl acetate | 12.25 |
| Ethyl butyrate | 26.20 |
| Isoamyl butyrate | 40.57 |

EXAMPLE X

100 Parts of the concentrate prepared in Example VIII is dissolved in 400 parts of propylene glycol and the mixture is added to a hard candy melt at the rate of 1.5 oz. of the concentrate solution per 100 lbs. of melt. After the finished candy has been produced, it is found to have an excellent strawberry flavor. When the candy is compared with candy made under the same conditions, but without the isopropyl-2-methyl-3-pentenoate prepared according to the process of Example III in the concentrate, it is found to have an inferior strawberry flavor.

EXAMPLE XI

A propylene glycol solution of the concentrate (1 part concentrate:4 parts of propylene glycol) as prepared in Example IX is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the isobutyl-2-methyl-3-pentenoic isomer mixture prepared according to the process of Example III.

EXAMPLE XII

The flavor concentrate prepared in Example IX is admixed with gum arabic in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the isobutyl-2-methyl-3-pentenoate isomer mixture prepared according to the process of Example III in the concentrate.

EXAMPLE XIII

The following mixture is prepared:

| Ingredient | Parts by Weight |
| --- | --- |
| Ethyl acetoacetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |
| Ethyl Heptanoate | 1 |
| Dulcinyl | 5 |
| 2(para-hydroxyphenyl)-3-butanone | 2 |
| Ethyl acetate | 1 |
| Beta-ionone | 10 |
| Palatone | 2 |
| Ethyl vanillin | 1 |
| Ethyl-3-methyl-3-phenyl glycidate | 150 |
| n-hexyl-2-methyl-3-pentenoate 3:2 cis:trans isomer mixture prepared according to the process of Example IV | 5 |

The n-Hexyl-2-methyl-3-pentenoate isomer mixture prepared according to the process of Example IV imparts a fruity, chamomile, peppery, floral note to this strawberry fragrance.

EXAMPLE XIV

Preparation of Soap Composition

One hundred grams of soap chips are mixed with one gram of the perfume composition of Example VI until a substantially homogeneous composition is obtained. The perfumed soap composition manifests an excellent raspberry character with a delicate raspberry topnote nuance.

EXAMPLE XV

Preparation of a Detergent Composition

A total of 100 g of a detergent powder is mixed with 0.15 g of the perfume composition of Example VI until a substantially homogeneous composition is obtained. This composition has an excellent raspberry fragrance.

EXAMPLE XVI

Preparation of a Cosmetic Powder Composition

A cosmetic powder is prepared by mixing in a ball mill 100 g of talcum powder with 0.25 g of n-hexyl-2-methyl-3-pentenoate 3:2 cis:trans isomer mixture prepared according to Example IV. It has an excellent fruity, chamomile aroma.

EXAMPLE XVII

Perfumed Liquid Detergent

Concentrated liquid detergents with a fruity, chamomile odor are prepared containing 0.10%, 0.15% and 0.20% of n-hexyl-2-methyl-3-pentenoate. They are prepared by adding and homogeneously mixing the appropriate quantity of n-hexyl-2-methyl-3-pentenoate in the liquid detergent. The detergents all possess a fruity, chamomile fragrance, the intensity increasing with greater concentration of n-hexyl-2-methyl-3-pentenoate isomer mixture.

EXAMPLE XVIII

Preparation of a Cologne and Handkerchief Perfume

Isopropyl-2-methyl-3-pentenoate 3:2 cis:trans isomer mixture prepared according to the process of Example III is incorporated in a cologne at a concentration of 2.5% in 85% aqueous ethanol; and into a handkerchief perfume at a concentration of 20% (in 95% aqueous ethanol). A distinct and definite strong fruity, herbaceous fragrance is imparted to the cologne and to the handkerchief perfume.

EXAMPLE XIX

Preparation of a Cologne and Handkerchief Perfume

The composition of Example XIII is incorporated in a cologne at a concentration of 2.5% in 85% aqueous ethanol; and into a handkerchief perfume at a concentration of 20% (in 95% aqueous ethanol). The use of the n-hexyl-2-methyl-3-pentenoate isomer mixture in the composition of Example XIII affords a distinct and definite strong strawberry aroma with a chamomile note to the handkerchief perfume and cologne.

EXAMPLE XX

Preparation of Soap Composition

One hundred grams of soap chips are mixed with one gram of n-hexyl-2-methyl-3-pentenoate 3:2 cis: trans isomer mixture until a substantially homogeneous composition is obtained. The perfumed soap composition manifests an excellent raspberry aroma with fruity and green notes and a chamomile nuance.

EXAMPLE XXI

Preparation of a Detergent Composition

A total of 100 g of a detergent powder is mixed with 0.15 g of the isomer mixture of 3:2 cis:trans ethyl-2-methyl-3-pentenoates of Example II until a substantially homogeneous composition is obtained. This composition has an excellent strawberry aroma with fruity and green notes and a chamomile nuance.

EXAMPLE XXII

Preparation of a Cosmetic Powder Composition

A cosmetic powder is prepared by mixing in a ball mill 100 g of talcum powder with 0.25 g of ethyl-2-methyl-3-pentenoate 3:2 cis:trans isomer mixture prepared according to Example II. It has an excellent fruity, green, strawberry character with a chamomile nuance. The same cosmetic powder is then further admixed in a ball mill with 0.25 g of isopropyl-2-methyl-3-pentenoate 3:2 cis:trans isomer mixture prepared according to Example III. The cosmetic powder now has an added herbaceous note.

EXAMPLE XXIII

Perfumed Liquid Detergent

Concentrated liquid detergents with green, fruity, strawberry notes and chamomile nuances are prepared containing 0.10%, 0.15% and 0.20% of ethyl-2-methyl-3-pentenoate 3:2 cis:trans isomer mixture prepared according to Example II. They are prepared by adding and homogeneously mixing the appropriate quantity of ethyl-2-methyl-3-pentenoate isomer mixture in the liquid detergent. The detergents all possess fruity, green, strawberry notes with chamomile nuances, the intensity increasing with greater concentrations of ethyl-2-methyl-3-pentenoate isomer mixture.

EXAMPLE XXIV

Preparation of a Cologne and Handkerchief Perfume

Ethyl-2-methyl-3-pentenoate 3:2 cis:trans isomer mixture prepared according to Example II is incorporated in a cologne at a concentration of 2.5% in 85% aqueous ethanol; and into a handkerchief perfume at a concentration of 20% (in 95% aqueous ethanol). A distinct, fruity, green, strawberry aroma with a chamomile nuance is imparted to the cologne and to the handkerchief perfume.

EXAMPLE XXV

Preparation of Mixture Containing 80% Cis-2-Methyl-3-Pentenoic Acid and 20% 2-Methyl-2-Pentenoic Acid

A. PREPARATION OF 3-PENTYN-2-OL

| | | |
|---|---|---|
| Equipment: | 5 liter reaction flask | |
| Material: | Methyl magnesium chloride (3 molar in tetrahydrofuran) | 3 liters |
| | Mapp gas (Mixture of methyl acetylene and allene) | 600 g |
| | Acetaldehyde (6 molar) | 264 g |

Procedure: Mapp gas is passed through a sodium hydroxide drying tube into the methyl magnesium chloride solution at 40°–50°C. The operation takes 5 hours to completion. The mixture is heated at 50°C for an additional 2 hours before cooling. To the cold solution is added 264 g of acetaldehyde at 20°–30°C over 2 hours with cooling. The mixture is then stirred for one hour at 25°C and is then decomposed with 800 ml of concentrated hydrochloric acid and 5 kg of ice. The resulting lower layer is extracted with one liter of benzene. The combined organic liquids are washed with two 200 ml portions of 20% aqueous NaCl and distilled at atmospheric pressure to a pot temperature of 92°C and then rushed over under vacuum. The rushed over material is then topped at 45–50 mm Hg. pressure to a pot temperature of 72°C. After the topping, this material is used to prepare 4-chloro-2-pentyne in part B, infra, without further purification.

B. PREPARATION OF 4-CHLORO-2-PENTYNE

| | | |
|---|---|---|
| Equipment: | 250 ml reaction flask | |
| Material: | 3-Pentyn-2-ol | 84 g (1 mole) |
| | Phosphorous trichloride | 69 g (0.5 mole) |

Procedure: The phosphorous trichloride is added at 20°–25°C with cooling to the 3-pentyn-2-ol prepared in part A, supra. The mixture is stirred for 12 hours at 20°–25°C and then heated to 72°C for 5 hours. IR analysis indicates that the reaction is complete. The material is then rushed over under vacuum to give 4-chloro-2-pentyne for the Grignard reaction exemplified in part C, infra. The yield is nearly quantitative.

C. PREPARATION OF 2-METHYL-3-PENTYNOIC ACID

| | | |
|---|---|---|
| Equipment: | 1 liter reaction flask | |
| Material: | 4-chloro-2-pentyne | 46 g (0.5 mole) |
| | Magnesium chips | 60 g (2.5 mole) |
| | Tetrahydrofuran (dry) | 500 ml |

Procedure: 4-Chloro-2-pentyne is dissolved in 200 ml of tetrahydrofuran and added over 4½ hours (after starting the reaction with iodine crystals) to the magnesium chips in 300 ml of tetrahydrofuran. The reaction temperature rises to 44°–50°C in the initiation period and is maintained at 28°–30°C with external cooling. The reaction mixture is allowed to stir for an additional hour after all of the 4-chloro-2-pentyne is added. The resulting Grignard reagent is poured onto 620 g of dry ice (powdered) with stirring. After the $CO_2$ evaporates, 300 ml of water is added and the solution is extracted with three 200 ml portions of toluene. The toluene extracts are discarded. The aqueous solution is cooled and acidified with 50 ml of concentrated hydrochloric acid; then extracted with two 200 ml portions of toluene. The toluene extract, after washing with three 50 ml portions of 20% NaCl solution is stripped of solvent and rushed over to give 22 g of crude acids.

The crude product is then fractionated in a semi-micro still to give 6.2 g of an acid mixture which contains a 3:1 mixture of 2-methyl-3-pentynoic acid and 2-methyl-2,3-pentadienoic acid.

D. HYDROGENATION REACTION

| Equipment: | Parr Shaker | |
|---|---|---|
| Material: | Mixture of 2-methyl-3-pentynoic acid and 2-methyl-2,3-pentadienoic acid | 4 g |
| | Methanol (absolute) | 50 ml |
| | 3% Pd/CaSO$_4$ | 0.1 g |

Procedure: The 2-methyl-3-pentynoic acid and 2-methyl-2,3-pentadienoic acid mixture produced in part C, supra is hydrogenated at room temperature in methanol in the presence of Pd/CaSO$_4$ catalyst at a hydrogen pressure of approximately 40 psig. The reaction is complete in 5 minutes. After removal of the methanol, the residue oil is analyzed by GLC which shows one peak. However, NMR analysis shows two products confirmed to be cis-2-methyl-3-pentenoic acid and 2-methyl-2-pentenoic acid (A 4:1 mixture).

EXAMPLE XXVI

Preparation of Mixture of 80% Ethyl-2-Methyl-3-Pentenoate and 20% Ethyl-2-Methyl-2-Pentenoate Into a 500 ml flask equipped with magnetic stirring bar, the following ingredients are added while maintaining the temperature at 20°–25°C using an ice water cooling bath and with stirring:

| (i) | Mixture of 80% cis-2-methyl-3-pentenoic acid and 20% 2-methyl-2-pentenoic acid (produced according to the process of Example XXV) | 38 g (0.33 moles) |
|---|---|---|
| (ii) | Ethyl bromide | 40 g (0.37 moles) |
| (iii) | Sodium hydroxide (50% aqueous solution) | 32 g (0.40 moles) |
| (iv) | Hexamethyl phosphoramide | 200 g |

The reaction mass is stirred for a period of 15 hours at room temperature. 300 ml water is then added to the mass and the solution is extracted with 200 ml of diethyl ether. The ether extract is washed with 20 ml of 20% sodium chloride solution, and is then concentrated by means of rotary evaporation. The resulting residue (32 grams) is distilled at 55 mm Hg. pressure with a semi-micro distillation apparatus, thereby giving 23 g of a mixture containing 80% cis-ethyl-2-methyl-3-pentenoate and 20% ethyl-2-methyl-2-pentenoate.

The mixture is separated using GLC trapping.

GLC Conditions:

Column: 20 feet × ¼ inch OD 5% OV-25 on 80/100 mesh Chromosorb G stainless steel
Flow: 100 ml/min Helium
Temperature:
    Column = 150° isothermal
    Injector = 230°
    Detector (T.C.) = 260°

The NMR analysis (CDCl$_3$) of the Cis isomer of ethyl-2-methyl-3-pentenoate is as follows:

| Signal | Interpretation |
|---|---|
| 1.22 (d, 3H) | —CH—C$\underline{H}_3$ |
| 1.28 (t, 3H) | —CH$_2$—C$\underline{H}_3$ |
| 1.66 (d, 3H) | C=CH—C$\underline{H}_3$ |
| 3.44 (m, 1H) | —C$\underline{H}$— |
| 4.15 (q, 2H) | O=C—O—C$\underline{H}_2$—CH$_3$ |
| 5.52 ppm (m, 2H) | —CH=CH— |

EXAMPLE XXVII

Preparation of Mixture Containing 80% Cis-n-Hexyl-2-Methyl-3-Pentenoate and 20% n-Hexyl-2-Methyl-2-Pentenoate Into a 125 ml reaction vessel equipped with magnetic stirrer, and maintained at room temperature, the following materials are added:

| (i) | Mixture of 80% cis-2-methyl-3-pentenoic acid and 20% 2-methyl-2-pentenoic acid prepared according to Example XXV | 1.1 g (0.01 moles) |
|---|---|---|
| (ii) | 1-Bromo hexane | 2.0 g (0.012 moles) |
| (iii) | Hexamethyl phosphoramide | 20 g |
| (iv) | Sodium hydroxide (50% aqueous solution) | 1.0 g (0.012 moles) |

The reaction mass is stirred for a period of three hours at room temperature. It is then diluted with 100 ml of water and extracted with 50 ml of diethyl ether. The resulting ether extract is washed with three 10 ml portions of 20% aqueous sodium chloride solution. The ether is then evaporated to yield 2.0 g of an oil. GLC trapping gives cis-n-hexyl-2-methyl-3-pentenoate having an NMR analysis (CDCl$_3$) as follows:

| Signal | Interpretation |
|---|---|
| 0.90 (t, 3H) | C$\underline{H}_3$—CH$_2$— |
| 1.24 (d, 3H) | CH$_3$—CH— |

| Signal | Interpretation |
|---|---|
| 1.28 (m, 6H) | —CH$_2$— |
| 1.64 (m, 5H) | —CH$_2$—C—O and =C—CH$_3$ |
| 3.44 (m, 1H) | —CH— |
| 4.08 (t, 2H) | —CH$_2$—O—C(=O) |
| 5.52 ppm (m, 2H) | —CH=CH— |

EXAMPLE XXVIII

Flavor Formulation Containing Mixture of 80% Cis-Ethyl-2-Methyl-3-Pentenoate and 20% Ethyl-2-Methyl-2-Pentenoate The following basic strawberry formulation is prepared:

| Ingredient | Parts by Weight |
|---|---|
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |
| Alpha-ionone | 0.0 |
| Gamma undecalactone | 0.2 |
| Diacetyl | 0.2 |
| Anethole | 0.1 |
| Cis-3-hexenol | 1.7 |
| 95% aqueous ethanol | 38.5 |
| Propylene glycol | 50.0 |
| | 100.0 |

To a portion of the foregoing formulation, 0.2% by weight of a mixture of 80% cis-ethyl-2-methyl-3-pentenoate and 20% ethyl-2-methyl-2-pentenoate prepared according to the process of Example XXVI is added. The formulation with the cis-ethyl-2-methyl-3-pentenoate is compared to the same formulation without said cis-ethyl-2-methyl-3-pentenoate.

Both flavors are evaluated in a milk beverage sweetened with 10% sugar at the rate of 100 ppm. Both beverages are tasted by an expert panel. The beverage containing the strawberry formulation *with* the addition of the mixture containing 80% cis-ethyl-2-methyl-3-pentenoate is unanimously preferred as having a more natural like, delicate strawberry aroma, a sweeter, more pleasant strawberry taste and a sweet, strawberry after-taste.

EXAMPLE XXIX

Raspberry Perfume Formulation

The following formulation is prepared:

| Ingredient | Parts by Weight |
|---|---|
| Mixture containing 80% cis-ethyl-2-methyl-3-pentenoate and 20% ethyl-2-methyl-2-pentenoate cis:trans prepared according to the process of Example XXVI | 10 |
| Ethyl-3-methyl-3-phenyl glycidate | 150 |
| Vanillin | 5 |
| 3-Hydroxy-2-methyl-4-pyrone | 10 |
| Beta-ionone | 30 |
| Ethyl acetate | 1 |
| Ethyl acetoacetate | 2 |
| Diacetyl | 1 |
| Heliotropyl Acetate | 50 |
| 4-(parahydroxyphenyl)-2-butanone | 50 |
| Ethyl laurate | 30 |
| Ethyl isovalerate | 10 |
| Ethyl butyrate | 50 |
| Cinnamyl cinnamate | 20 |
| | 419 |

The mixture containing the cis-ethyl-2-methyl-3-pentenoate imparts to this raspberry perfume formulation a delicate raspberry topnote nuance.

EXAMPLE XXX

Tobacco Flavor Formulation and Tobacco

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the mixture containing 80% cis ethyl-2-methyl-3-pentenoate and 20% ethyl-2-methyl-2-pentenoate produced according to the process of Example XXVI. The control cigarettes not containing the mixture having 80% cis-ethyl-2-methyl-3-pentenoate produced according to the process of Example XXVI and the experimental cigarettes which do contain the mixture having 80% cis-ethyl-2-methyl-3-pentenoate produced according to the process of Example XXVI are evaluated by paired comparison, and the results are as follows:

In aroma, the cigarettes containing the mixture having 80% cis-ethyl-2-methyl-3-pentenoate have been found to be more aromatic.

In smoke flavor, the cigarettes containing the mixture having 80% cis-ethyl-2-methyl-3-pentenoate are more aromatic, more sweet, more bitter, slightly less harsh in the mouth and throat and leave a slight, sweet chemical mouth-coating effect similar to Turkish tobacco.

In summary, the mixture having 80% cis-ethyl-2-methyl-3-pentenoate enhances the tobacco-like taste and aroma of a blended cigarette and imparts to that cigarette a Turkish-like character in smoke flavor.

EXAMPLE XXXI

The following mixture is prepared:

| Ingredient | Parts by Weight |
|---|---|
| Ethyl acetoacetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |
| Ethyl heptanoate | 1 |
| Dulcinyl | 5 |
| 2(para-hydroxyphenyl)-3-butanone | 2 |
| Ethyl acetate | 1 |
| Beta-ionone | 10 |
| Palatone | 2 |
| Ethyl vanillin | 1 |
| Ethyl-3-methyl-3-phenyl glycidate | 150 |
| Mixture containing 80% cis-n-hexyl-2-methyl-3-pentenoate (prepared according to the process of Example XXVII) | 5 |

The mixture containing 80% cis-ethyl-2-methyl-3-pentenoate isomer mixture prepared according to the process of Example XXVII imparts a fruity, chamomile, peppery, floral note to this strawberry fragrance.

EXAMPLE XXXII

Preparation of Soap Composition

One hundred grams of soap chips are mixed with one gram of the perfume composition of Example XXIX until a substantially homogeneous composition is obtained. The perfumed soap composition manifests an excellent raspberry character with a delicate raspberry topnote nuance.

EXAMPLE XXXIII

Preparation of a Detergent Compostion

A total of 100 g of a detergent powder is mixed with 0.15 g of the perfume composition of Example XXIX until a substantially homogeneous composition is obtained. This composition has an excellent raspberry fragrance.

EXAMPLE XXXIV

Preparation of a Cosmetic Powder Composition

A cosmetic powder is prepared by mixing in a ball mill 100 g of talcum powder with 0.25 g of the mixture containing 80% cis-n-hexyl-2-methyl-3-pentenoate prepared according to Example XXVII. It has an excellent fruity, chamomile aroma.

EXAMPLE XXXV

Perfumed Liquid Detergent

Concentrated liquid detergents with a fruity, chamomile odor are prepared containing 0.10%, 0.15% and 0.20% of the mixture having 80% cis-n-hexyl-2-methyl-3-pentenoate prepared according to Example XXVII. They are prepared by adding and homogeneously mixing the appropriate quantity of mixture containing 80% cis-n-hexyl-2-methyl-3-pentenoate in the liquid detergent. The detergents all possess a fruity, chamomile fragrance, the intensity increasing with greater concentration of mixture containing 80% cis-n-hexyl-2-methyl-3-pentenoate.

EXAMPLE XXXVI

Preparation of a Cologne and Handkerchief Perfume

The composition of Example XXXI is incorporated in a cologne at a concentration of 2.5% in 85% aqueous ethanol; and into a handkerchief perfume at a concentration of 20% (in 95% aqueous ethanol). The use of the mixture containing 80% cis-n-hexyl-2-methyl-3-pentenoate in the composition of Example XXXI affords a distinct and definite strong strawberry aroma with a chamomile note to the handkerchief perfume and cologne.

EXAMPLE XXXVII

Preparation of Soap Composition

One hundred grams of soap chips are mixed with one gram of mixture containing 80% cis-n-hexyl-2-methyl-3-pentenoate of Example XXVII until a substantially homogeneous composition is obtained. The perfumed soap composition manifests an excellent raspberry aroma with fruity and green notes and a chamomile nuance.

EXAMPLE XXXVIII

Preparation of a Detergent Composition

A total of 100 g of a detergent powder is mixed with 0.15 g of the mixture containing 80% cis-ethyl-2-methyl-3-pentenoate of Example XXVI until a substantially homogeneous composition is obtained. This composition has an excellent raspberry aroma with fruity and green notes and a chamomile nuance.

What is claimed is:

1. A process for preparing a mixture containing 80% cis-2-methyl-3-pentenoic acid $C_2$–$C_6$ alkyl ester and 20% 2-methyl-2-pentenoic acid $C_2$–$C_6$ alkyl ester comprising the steps of:

a. reacting in the presence of a non-reactive solvent at a temperature in the range of 40°–60°C methyl acetylene with a methyl magnesium halide to form a methyl acetylene magnesium halide Grignard reagent;

b. reacting in the presence of a non-reactive solvent at a temperature in the range of 20°–30°C the methyl acetylene magnesium halide Grignard reagent with acetaldehyde to form a 3-pentyn-2-ol magnesium halide salt;

c. hydrolyzing said 3-pentyn-2-ol magnesium halide salt with concentrated mineral acid to form 3-pentyn-2-ol;

d. reacting said 3-pentyn-2-ol with a halogenating reagent selected from the group consisting of phosphorous trichloride, phosphorous tribromide and $SOCl_2$ at a temperature in the range of 20°–80°C to form a 4-halo-2-pentyne;

e. reacting in the presence of a non-reactive solvent at a temperature in the range of 25°–50°C said 4-halo-2-pentyne with magnesium to form a 4-magnesium halo-2-pentyne Grignard reagent;

f. reacting said 4-magnesium halo-2-pentyne Grignard reagent with $CO_2$ to form a magnesium halo carboxylate salt mixture;

g. hydrolyzing said magnesium halo carboxylate salt mixture with aqueous mineral acid at a temperature in the range of 20°–30°C to form a mixture of 2-methyl-3-pentenoic acid and 2-methyl-2,3-pentadienoic acid;

h. reacting in the presence of a non-reactive solvent said mixture of 2-methyl-3-pentynoic acid and 2-methyl-2,3-pentadienoic acid with hydrogen; the reaction taking place at a pressure of 20–200 psig and a temperature in the range of 20°–40°C in the presence of a Pd/CaSO$_4$ catalyst to form a mixture containing 80% cis-2-methyl-3-pentenoic acid and 20% 2-methyl-2-pentenoic acid; and i. intimately admixing said mixture of 80% cis-2-methyl-3-pentenoic acid and 2-methyl-2-pentenoic acid with an alkali metal base and a compound having the formula RX, wherein R is $C_2$–$C_6$ alkyl, and X is selected from the group consisting of chloro, bromo and iodo in the presence of a solvent selected from the group consisting of hexamethyl phosphoramide, a dilower alkyl formamide and dimethyl sulfoxide at a temperature in the range of 0°–50°C.

\* \* \* \* \*